(12) United States Patent
Bagwell et al.

(10) Patent No.: US 9,259,564 B2
(45) Date of Patent: Feb. 16, 2016

(54) ENTERAL FEEDING ASSEMBLY WITH LOCK ASSEMBLY

(75) Inventors: Alison S. Bagwell, Alpharetta, GA (US); Stephen A. Baratian, Roswell, GA (US); Thomas G. Estes, Atlanta, GA (US); Emily A. Reichart, Atlanta, GA (US); John A. Rotella, Roswell, GA (US); Jonathan P. Bauer, Cincinnati, OH (US); Jeremy L. Hemingway, Cincinnati, OH (US)

(73) Assignee: Avent, Inc., Alpharetta, GA (US)

( * ) Notice: Subject to any disclaimer, the term of this patent is extended or adjusted under 35 U.S.C. 154(b) by 436 days.

(21) Appl. No.: 12/640,598

(22) Filed: Dec. 17, 2009

(65) Prior Publication Data

US 2010/0185159 A1     Jul. 22, 2010

Related U.S. Application Data

(60) Provisional application No. 61/146,577, filed on Jan. 22, 2009.

(51) Int. Cl.
*A61M 25/16* (2006.01)
*A61M 39/10* (2006.01)
*A61J 15/00* (2006.01)

(52) U.S. Cl.
CPC ........ *A61M 39/1055* (2013.01); *A61J 15/0065* (2013.01); *A61J 15/0092* (2013.01); *A61J 15/0015* (2013.01); *A61J 15/0026* (2013.01); *A61J 15/0042* (2013.01); *A61M 2039/1094* (2013.01); *A61M 2202/0482* (2013.01); *A61M 2205/6045* (2013.01)

(58) Field of Classification Search
CPC ............... A61M 39/10; A61M 39/20; A61M 2205/6045; A61M 2205/0482; A61M 2039/1094; A61J 15/0015; A61J 15/0092; A61J 15/0065; A61J 15/0026
USPC .................................... 604/533–534, 164.01
See application file for complete search history.

(56) References Cited

U.S. PATENT DOCUMENTS

| 4,944,732 | A |   | 7/1990  | Russo |
|-----------|---|---|---------|-------|
| 5,273,529 | A | * | 12/1993 | Idowu ........................... 604/500 |
| 5,425,708 | A |   | 6/1995  | Nasu |
| 5,833,275 | A | * | 11/1998 | Andersen ...................... 285/305 |
| 6,019,746 | A |   | 2/2000  | Picha et al. |

(Continued)

FOREIGN PATENT DOCUMENTS

| JP | 11-115641 A   | 4/1999 |
| JP | 2000-009117 A | 1/2000 |
| WO | WO 95/18640 A1 | 7/1995 |

*Primary Examiner* — Edelmira Bosques
(74) *Attorney, Agent, or Firm* — Dority & Manning, P.A.

(57) ABSTRACT

There is provided an enteral feeding assembly having a base and a connector. The base has a catheter with a lumen for communication with a body lumen. The base also has an opening with a predetermined shape on its proximal side that also communicates with the catheter lumen. The connector has a key configured to complement the predetermined shape of the opening in the base, which occurs desirably in one position only, so that the connector and base may be joined together. The connector is also connected to a feeding tube that provides a nutrient solution from a replaceable feeding bag. Once the connector is in position in the base, liquid may from the bag to the body lumen. Once in position, the connector may rotate 360 degrees relative to the base before being again in the installation/removal position.

11 Claims, 10 Drawing Sheets

(56) References Cited

U.S. PATENT DOCUMENTS

| | | | |
|---|---|---|---|
| 6,419,670 B1* | 7/2002 | Dikeman | 604/533 |
| 2003/0120260 A1* | 6/2003 | Chu et al. | 604/533 |
| 2003/0158539 A1 | 8/2003 | Bouphavichith | |
| 2005/0124935 A1 | 6/2005 | McMichael | |
| 2006/0111688 A1* | 5/2006 | Kraus et al. | 604/415 |
| 2008/0140055 A1 | 6/2008 | Shirley | |

* cited by examiner

ENTERAL FEEDING ASSEMBLY WITH LOCK ASSEMBLY

This application claims the benefit of U.S. provisional application 61/146,577, filed Jan. 22, 2009.

BACKGROUND

This disclosure relates generally to improved medical care for patients who require enteral feeding. More particularly, it relates to an enteral feeding assembly having a novel locking assembly which permits a user or health care provider to close or lock and to open or unlock, access to a catheter of the enteral feeding assembly.

Numerous situations exist in which a body cavity needs to be catheterized to achieve a desired medical goal. One relatively common situation is to provide nutritional solutions or medicines directly into the stomach or intestines. A stoma is formed in the stomach or intestinal wall and a catheter is placed through the stoma. Feeding solutions can be injected through the catheter to provide nutrients directly to the stomach or intestines (known as enteral feeding). A variety of different catheters intended for enteral feeding have been developed over the years, including some having a "low profile" relative to the portion of the catheter which sits on a patient's skin, as well as those having the more traditional or non-low profile configuration. U.S. Pat. No. 6,019,746 provides an example of such a device.

As indicated above, there are a variety of instances in which it may be necessary to use a catheter, one of which is the not uncommon reaction following major surgery in which a patient's stomach function is impaired for a period of time. In addition to the need to supply or supplement the body with a certain level of nutrients and the like following surgery as well as in other instances of impaired or limited gastric functionality, a further issue is that an unfed gut can become a source of bacteria that gets into the bloodstream. These types of problems may be resolved by the introduction of nutrients through an enteral feeding device tube properly inserted through the patient's abdominal wall, gastric wall, pylorus, duodenum, and/or into the jejunum beyond the Ligament of Treitz.

A problem universal to low profile and non-low profile enteral feeding devices or enteral feeding assemblies is the difficulty in connecting and disconnecting the feeding tube to and from the base assembly. Many prior art enteral feeding base assemblies "EFA", such as the one shown, for example, in cross-section in FIG. 1, have a low profile base B and a catheter C which extends through the base and a distance from the base. A distal end of the catheter of such a device/assembly often includes a balloon which may be expanded to hold the catheter in a position in a body lumen, such as a stomach lumen. Such an enteral feeding device/assembly also often has a plug "P" attached to the low profile or non-low profile device by a tether "T."

Changing a feeding tube involves disconnecting the prior tube, or removing the plug P from the base, and connecting a new tube in its place. This can be a surprisingly difficult exercise, especially if the patient is overweight, which can limit the visibility of the base from the patient himself, or young, since it is often necessary or desirable to change the assembly while the patient is sleeping. The turning on of a light during the night can wake the patient. Yet, without being sure that the new tube is correctly connected, there is a risk of the leaking of gastric contents onto a patient's skin surface, clothing, and so forth. There is also a similar risk of the leaking of the feeding solution. Further, when the connector sits tightly within the base, it may be difficult to remove, thereby requiring extensive pulling, movement of the connector and base and even unwanted displacement of the base.

Accordingly, there is a need for an enteral feeding assembly and connector which permits a user or health care provider a way to easily change the enteral feeding tube. Such a system would permit a user or health care provider to easily and reliably disconnect the previous, used, feeding connector and connect a new feeding connector, desirably without needing to see the base.

SUMMARY

In response to the difficulties and problems discussed herein, an enteral feeding assembly is provided. The enteral feeding assembly includes a base having a catheter positioned through the base forming an opening therein. A portion of the catheter extends away from the base. The enteral feeding assembly further includes a connector with a key configured to engage at least a portion of the base to move the assembly into the open position and the closed position.

In another aspect, there is provided an enteral feeding assembly with a lock assembly having a base and a connector for a feeding set. The base has a proximal side and a distal side and includes a catheter with a lumen positioned through the base. A portion of the catheter extends away from the base on the distal side. The base has an opening in the proximal side. The connector has a tube for the supply of a feeding solution to the lumen of the catheter once the connector and base are connected. The connector has a key configured to engage the opening in the base and to enter the base to allow the connection of the base and feeding set such that the tube and the lumen are in fluid communication.

The base is desirably a low profile base configured to be positioned on the skin surface of a patient.

A number of different shapes for the key or flange of the connector may be used. There are embodiments in which the key has one axis of symmetry, like that of an arrowhead. Alternatively the key may have no axis of symmetry.

The connector generally includes a cuff configured to open a valve within the base to allow the nutrient solution to flow from the replaceable feeding bag to the patient. The valve closes upon withdrawal of the connector and its cuff so that there is no leakage from the base. The connector may rotate up to 360 degrees after connection to the base.

The enteral feeding assembly may also include at least one detent within the base positioned to contact or interact with the key to provide a tactile indication of a position of the key within the base and retard the movement of the key. The connector may rotate in either direction between 300 and 345 degrees after connection to the base, prior to contacting the detent. The connector may also rotate up to 360 degrees after connection to the base by overcoming the restraining force of the detent.

Also provided is a method of using a lock assembly with an enteral feeding assembly. The steps include providing an enteral feeding assembly, including a base configured to be disposed on a skin surface of a patient. The base has a distal surface configured to be positioned adjacent a skin surface, the base including a proximal surface having an opening. The base includes a catheter having a lumen formed therethrough which is in communication with the opening in the base, a portion of the catheter extending distally away from the distal surface of the base, at least a portion of the distal end of the catheter configured to be positioned in a body lumen. The steps further include providing a feeding set connector with a flange having a predetermined shape and a cuff extending from the flange. There is an opening formed through the feeding set connector, flange and cuff. The flange is positioned through the opening having the predetermined shape. The flange is moved so that at least a portion of the flange is in a position in the space below the proximal surface of the base. The flange is locked into a position relative to the base with the cuff extending through the opening in the base and in liquid communication with the lumen of the catheter, so that liquid nutrients in liquid communication with the feeding set connector move therethrough and through the catheter lumen to a body lumen. The method may also include the step of un-locking the flange and removing the feeding set connector from the base.

DETAILED DESCRIPTION

Figure 1:
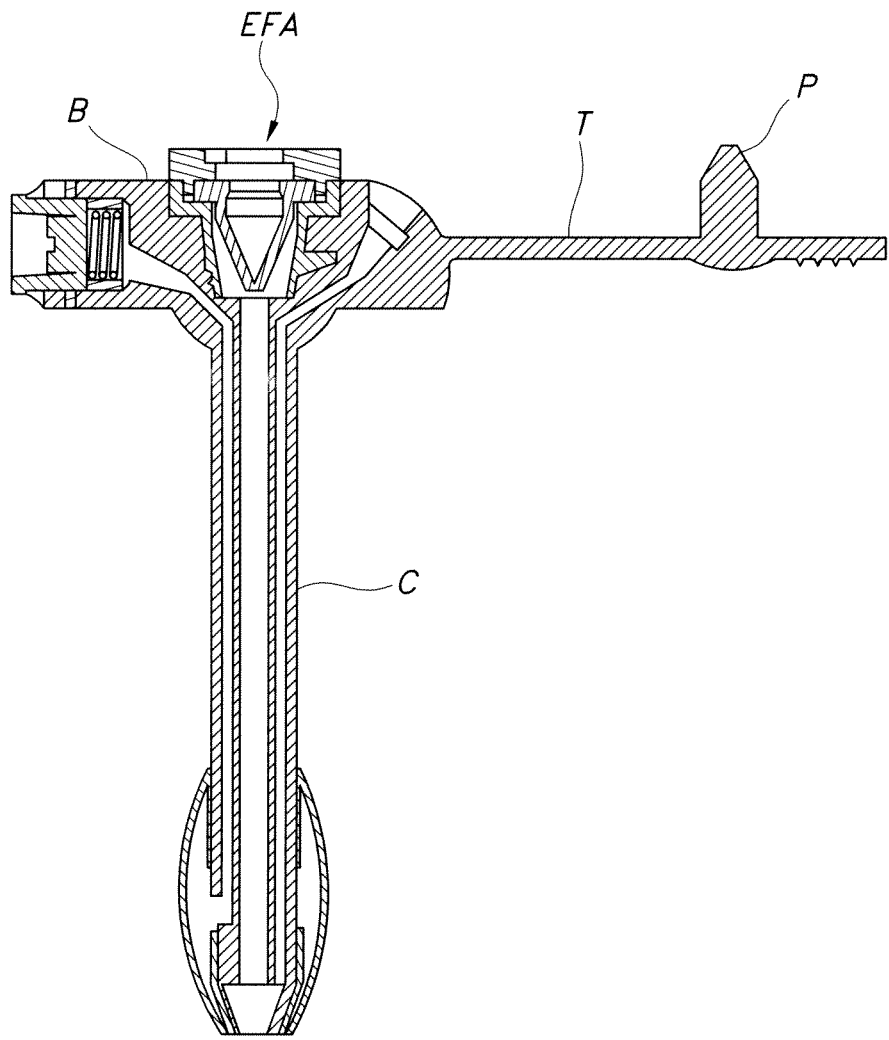
FIG. 1 is a side view of a prior art enteral feeding assembly, showing a base and attached catheter, and a plug used to close an opening which provides access to the catheter, the plug coupled to the base by a tether.

Reference will now be made in detail to one or more embodiments, examples of which are illustrated in the drawings. It should be understood that features illustrated or described as part of one embodiment may be used with another embodiment to yield still a further embodiment. It is intended that the claims include these and other modifications and variations as coming within the scope and spirit of the disclosure.

Turning now to the drawings, it will be understood that the prior art is illustrated in FIG. 1 and has been described above. One embodiment, according to this disclosure, of an enteral feeding assembly 110 with a lock assembly is shown in FIGS. 2 and 5-7. Other embodiments shall also be described below.

Figure 2:
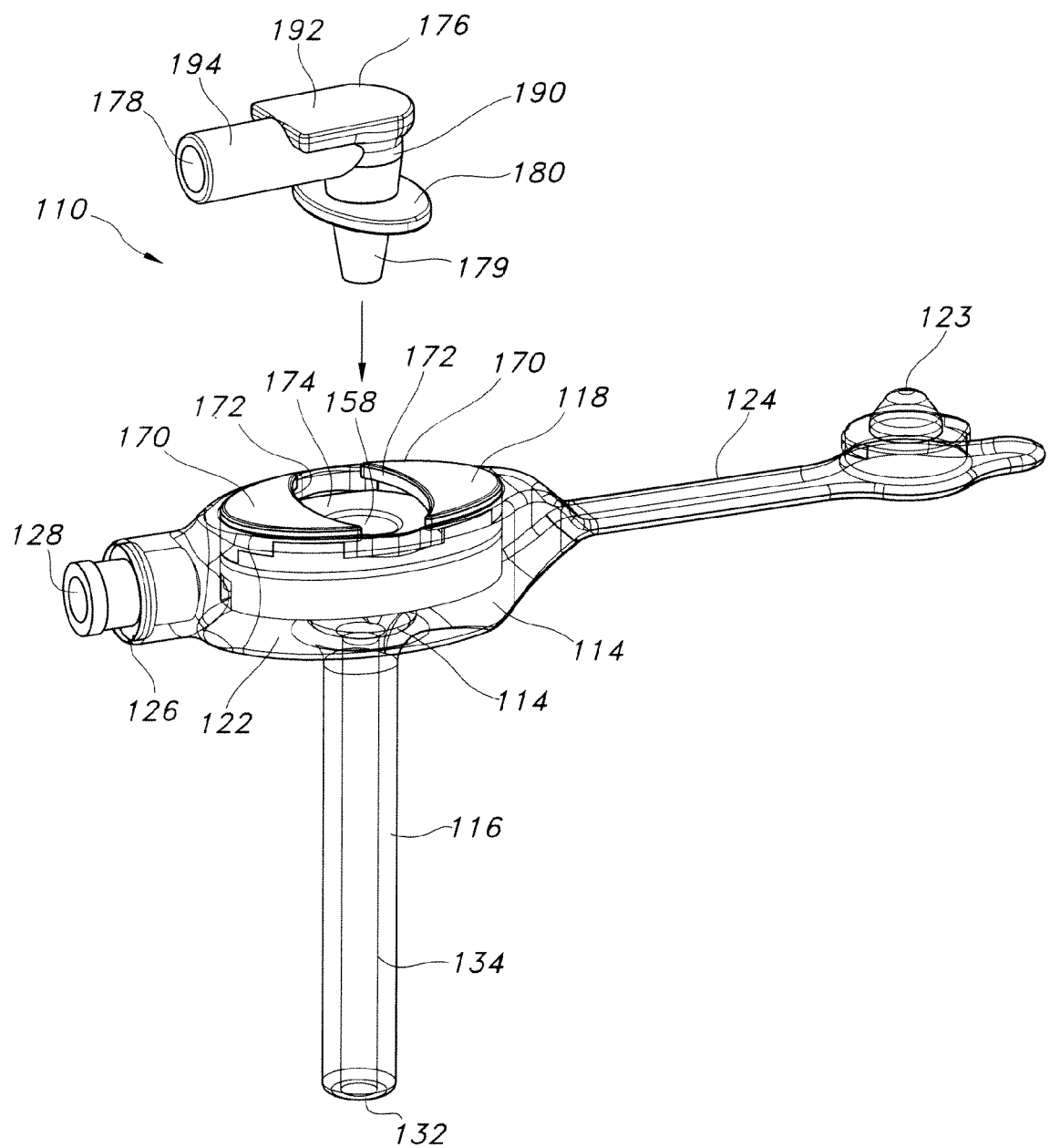
FIG. 2 is a perspective view of an enteral feeding assembly according to this disclosure, having a low-profile base and a catheter positioned to extend from the base, a lock assembly including a key opening on a proximal surface of the base and a feeding set connector having a matching key.
Figure 3:
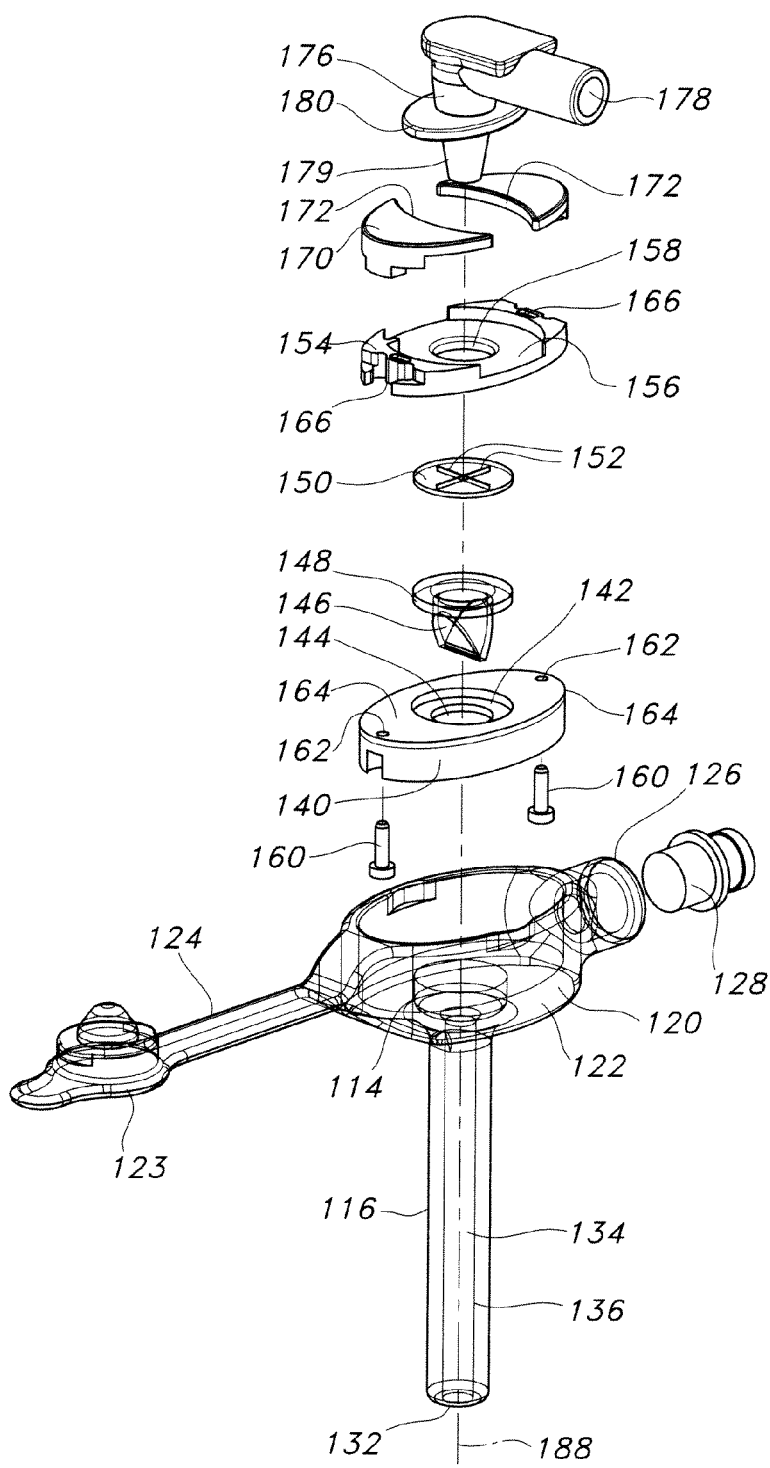
FIG. 3 is an exploded perspective view of the enteral feeding assembly base and connector of FIG. 2.

As illustrated in FIGS. 2-7, an enteral feeding assembly 110 is provided. The enteral feeding assembly 110 includes a base 114 and a catheter 116 carried by the base 114, as best shown in FIGS. 2 and 3. The base 114 has a proximal surface 118 and a distal surface 120. The distal surface 120 is positioned against or adjacent a patient's skin, when the assembly 110 is positioned for operation, as described in detail below. The base 114 includes a perimeter 122 having a plug 123 attached to a tether 124. The base 114 also includes a side access port 126 which may also include a barrier (not shown) and/or a closure plug 128.

The catheter 116 may be positioned partially through the base 114 such that the catheter 116 has an open proximal end (not shown) which may be positioned internally with respect to the base 114 and an open distal end 132 with extends a distance from the distal surface 120 of the base 114. As shown in FIG. 3, the catheter 116 desirably has at least one lumen or a first lumen 134 (a feeding lumen) formed therethrough, and may include a second lumen 136 (an inflation lumen) which may be formed within a portion of the first lumen 134.

The second lumen 136, at a distal end (not shown), is desirably in communication with a retainer, such as, for example, a sleeve of balloon (not shown). At a proximal end 138, the second lumen 136 is desirably in communication with the barrier (not shown) and/or side access port 126, to permit air or liquid to be introduced through barrier or side access port 126 to the second lumen 136 and into the sleeve or balloon which may provide the retainer (not shown). Alternatively, however, the catheter 116 may include a non-inflatable retainer (not shown). In this alternative, the second lumen, and/or a side access port may be unnecessary, and may not be included in such an embodiment (not shown).

As illustrated in FIG. 3, the base 114 further includes an inner mount 140 which is positioned within the base 114. The inner mount 140 includes a recessed plate 142 having an opening 144 therethrough. The opening 144 is in communication with the proximal end (not shown) of the catheter 116. A valve 146, desirably a duckbill valve, having a mounting collar 148 is provided. The collar 148 is positioned proximally on the recessed plate 142 of the inner mount 140 such that the valve 146 extends through the opening 144 and into the open proximal end (not shown) of the catheter 116. It will be understood that the valve 146 is positioned in a closed position until it is urged open. In addition, a diaphragm 150 having at least one, and desirably, a plurality of slits 152 therein is desirably positioned proximally over the mounting collar 148 and in alignment with the valve 146.

A locking mount 154 is positioned proximally relative to the valve 146, the diaphragm 150, and the inner mount 140. The locking mount 154 includes a recessed locking plate 156 having an opening 158 positioned therethrough which is in alignment with the opening 144 of the inner mount 140.

The inner mount 140 may include a pair of pins 160, each of which extends through an aperture 162 positioned on opposing ends 164 of in the inner mount 140. The pins 160 desirably extend into and may couple to opposing ends 166 of the locking mount 154.

A pair of mount covers 170 is positioned over each end 166 of the locking mount 154. The pins 160 may extend through the locking mount 154 such that one pin 160 couples to each mount cover 170. Alternatively, the mount covers 170 may be adhesively coupled to the locking mount 154. The locking mount 154 and the mount covers 170 cooperate to provide the proximal surface 118 of the base 114. A portion of the edges 172 of the mount covers 170 cooperate to form a "key hole"

or opening 174 which may provide a configuration, or a predetermined shape. In this embodiment, the edges 172 cooperate to form a generally elliptical-shaped opening 174. Depending on the embodiment, the mount covers 170 may be a single piece; e.g. FIG. 13, discussed below.

Figure 6:
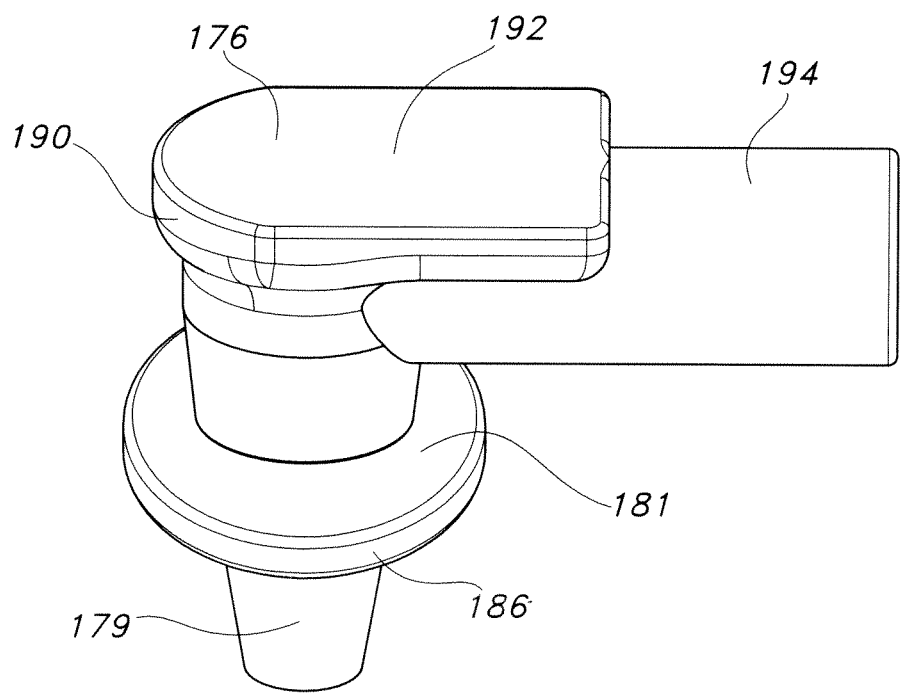
FIG. 6 is an upper perspective view of the feeding set connector of FIGS. 2-5, showing a flange which provides the key.
Figure 7:
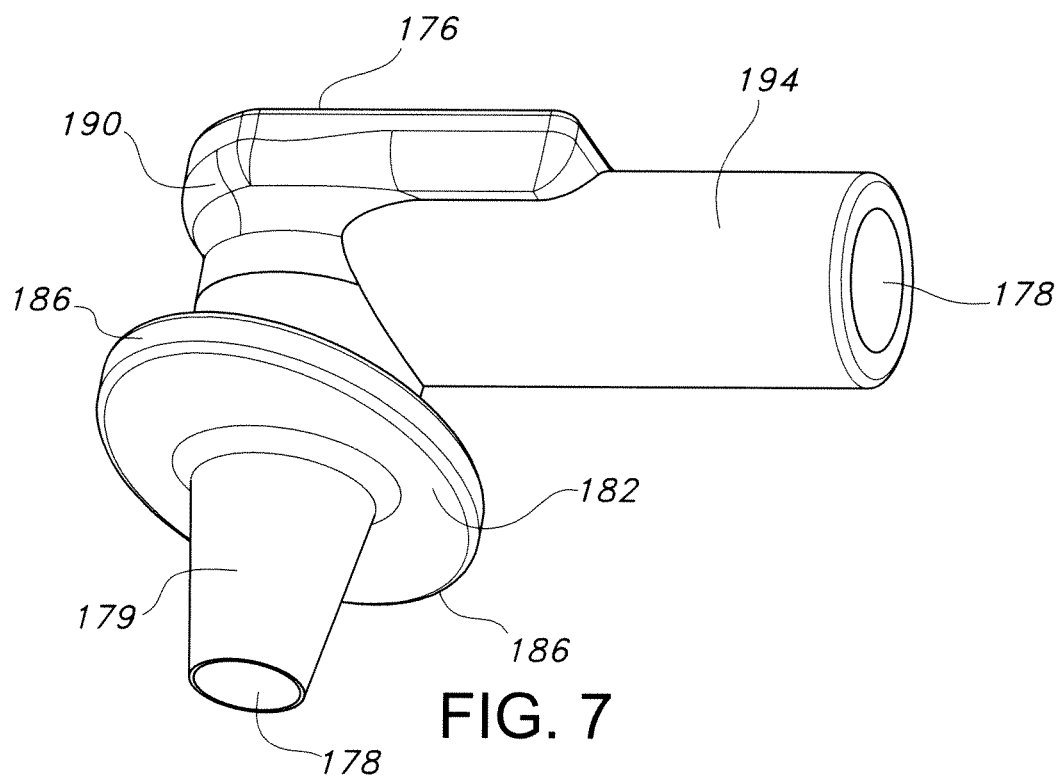
FIG. 7 is a lower perspective view of the feeding set connector of FIGS. 2-5, showing the flange which provides the key.

A feeding set (not shown) has a replaceable bag that holds a nutrient solution, connected by tubing to a feeding set connector 176, as illustrated best in FIGS. 6 and 7. The feeding set connector 176 desirably has an opening or port 178 formed therethrough. The feeding set connector 176 desirably includes a cuff 179 or similar apparatus (such as a portion of a catheter, cannula, and so forth). The port 178 also desirably extends through the cuff 179 or similar apparatus, the cuff 179 is configured to desirably extend through the opening 174 of the mount covers 170, through the opening 158 of the locking mount 154, through the slits 153 of the diaphragm 150, through the opening 144 in the inner mount 140, and through the valve 146 to communicate with the lumen 134 of the catheter 116 at the open proximal end (not shown) thereof (FIG. 3). The feeding set connector 176 also includes a flange 180 having a predetermined shape which desirably is adapted to fit into the opening 174 having a predetermined shape. Once the connector 176 is in position on the base 114, the tubing of the feeding set is in fluid communication with the lumen of the catheter so that nutrients may be delivered to the patient.

As shown in the embodiment of FIGS. 2-7, the flange is an elliptically-shaped flange 180 which fits through the elliptical-shaped opening 174 provided by the mount covers 170. The feeding set connector 176 is desirably coupled to or formed with the flange 180 and is positioned on a proximal surface 181 of the flange 180. The cuff 179 is desirably positioned to extend from a distal surface 182 of the flange 180 and the opening or port 178 extends through the feeding connector set 176, the flange 180 and the cuff 179. The elliptically-shaped flange 180 fits between the perimeter edges 172 the mount covers 170 which form the opening 174 therethrough.

For use, the flange 180 is desirably positioned on the space below the opening 174 provided by the recessed locking plate 156 of the locking mount 154. It will be understood that the recessed locking plate 156 provides a space below the proximal surface 118 formed by the mount covers 170 of the base 114. The recessed locking plate 156 which provides the space desirably provides a diameter which is greater than the diameter of the opening 174 provided by the mount covers 174, and the opening 158 provided within the recessed locking plate 156. The flange 180 is then rotated clockwise and/or counter clockwise to an angle of, for example, desirably about 90 degrees, until each end 186 of the flange 180 is positioned under one of the mount covers 170. In this position, the flange 180 desirably releasably locks into a fixed position on the locking plate 156.

Figure 4:
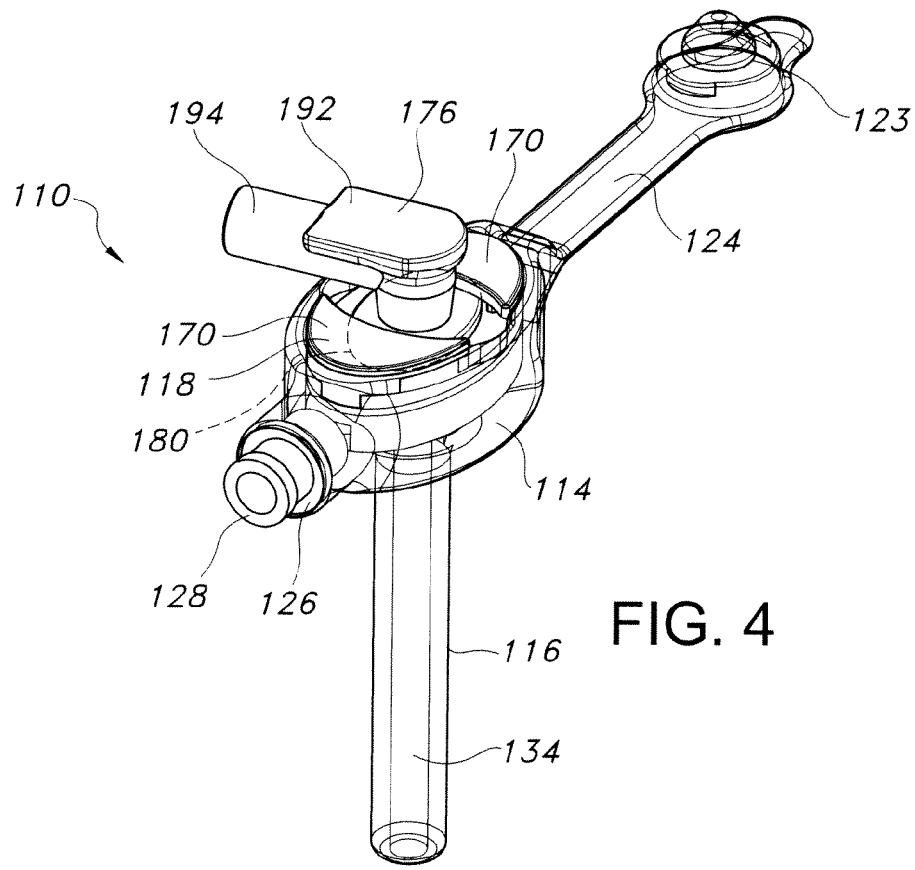
FIG. 4 is a perspective view similar to FIG. 2, but showing the flange or key of the feeding connector set positioned within the base key opening.
Figure 5:
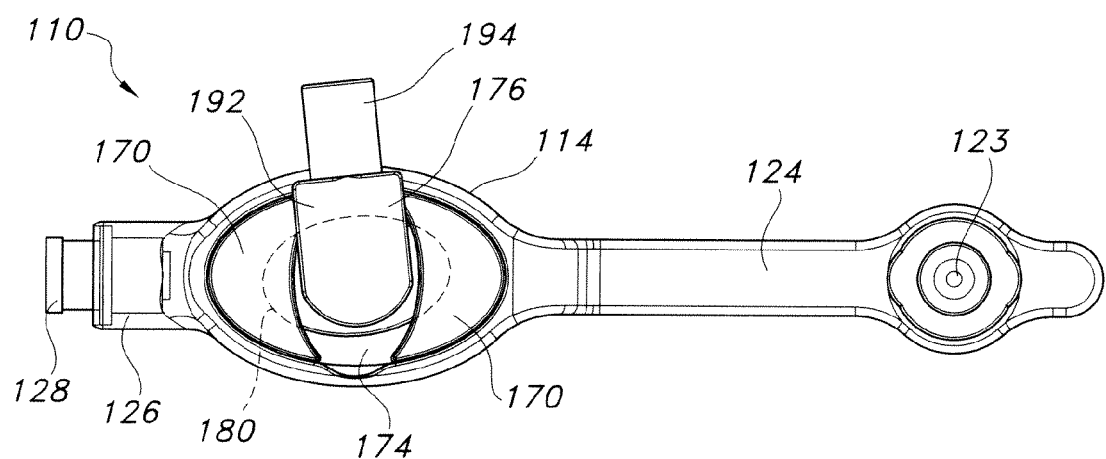
FIG. 5 is an upper plan view of FIG. 4.

Once the flange 180 is inserted into the space provided by the recessed locking plate 156, as shown in FIGS. 4 and 5, the cuff 179 is positioned through the aforementioned structures so that the cuff 179, feeding set connector 176, and feeding set (not shown) are in fluid communication with the lumen 134 of the catheter 116 of the enteral feeding assembly 110. Desirably, the feeding set connector 176 is configured to rotate or pivot about an axis 188 (FIG. 3), to permit movement of a portion of the feeding set connector 176. This movement does not affect the locked position of the feeding set connector 176 to the base 114, and it relieves pressure on the enteral feeding assembly 110 and/or the feeding set (not shown) from the tubing.

The feeding set connector 176 may include a base 190 having a thumb landing 192 thereon, as shown in FIGS. 6 and 7. The feeding set connector 176 desirably has at least a portion 194 of a feeding catheter attached thereto and which is in communication with the port 178. The portion 194 of the feeding catheter may include a length of catheter (not shown) which may couple to a feeding bag (not shown). Alternatively, the portion 194 of the feeding catheter may terminate in a connector (not shown) which may couple to a feeding catheter which is coupled or adapted to couple to a feeding bag.

In a method of use, as shown generally in FIGS. 2-7, the enteral feeding assembly 110 is provided, such that the catheter 116 is positioned through a stoma of a patient and a portion of the catheter extends into a body lumen of the patient, such as a stomach lumen (not shown). The catheter 116 and enteral feeding assembly 110 are desirably held within the stomach lumen by a retainer (not shown) positioned on a distal end 110 of the catheter 116. The distal surface 120 of the enteral feeding assembly 110 is positioned against or adjacent the patient's abdominal skin. The plug 123 on the tether 124 is desirably removed from its position in the opening 158 of the locking mount 154 (thereby blocking any gastric fluid from being emitted therefrom). The feeding set connector 176 with the flange 180 and cuff 179 with the port 178 formed therethrough are positioned such that the elliptical shape of the flange 180 is aligned with the elliptical opening 174 formed by the mount covers 170. The flange 180 is then moved through the opening 174 and rotated, desirably about ninety (90) degrees either clockwise or counter-clockwise, so that each end 186 of the flange 180 is positioned under one of the mount covers 170. The ends 186 contact the lower surface of the proximal side of the base once the flange 180 is turned. In this position, the flange 180 desirably remains in position, referred to herein as "locked", until actively released by a patient or health care provider.

When the flange 180 moves through the opening 174 provided between the mount covers 170, the cuff 179 simultaneously moves through the opening 158 in the locking mount 154, through the slits 152 in the diaphragm 150, through the opening 142 in the inner mount 140 and through the valve 146 thereby opening the valve 146, so that the cuff 179 and port 178 therein is in communication with the open proximal end (not shown) of the catheter 116. In this manner, liquid nutrients from a feeding bag (not shown) coupled to or provided through a tube with the feeding set (not shown) may pass therethrough and through the feeding set connector 176, through the lumen 134 of the catheter 116, and into the patient's stomach lumen.

When it is desired to remove the feeding set connector 176 from the base, for example to change the feeding bag and connector, the flange 180 is rotated to align with the opening 174 provided by the mount covers 170. The connector 176 is gently urged upward away from the base 114, withdrawing the flange 180 through the opening 174. Simultaneously, the cuff 179 provided with the flange 180 moves out of the open proximal end (not shown) of the catheter 116 and out of the valve 146 thereby permitting the valve 146 to close, through the opening 144 in the locking mount 140, and through the slits 152 of the diaphragm 150. The diaphragm 150 and the valve 146 close the catheter 116 so that the nutrients provided to the patient's stomach lumen are retained therein. The cuff 179 continues to move through the opening 158 in the locking mount 154 and through the opening 174 created between the mount covers 170. At this point, the disconnection between the feeding set connector 176 and the enteral feeding assembly 110 is completed.

The opening 174 provided between the mount covers 172 desirably provides communication through the opening 158 in the locking mount 156, the opening 144 in the inner mount 140, through the slits 152 of the diaphragm (when opened) and through the valve 146 (when opened) to at least the first lumen 134 of the catheter 116.

The combination of the flange 180 of the feeding set connector 176 and the configuration of the locking mount 154, mount covers 170, and other apparatus provide a locking assembly for the enteral feeding assembly 110. Specifically, the opening 174 desirably provides a predetermined, shaped "key-hole," while the space created by the recessed locking plate 156 holds the "key." The flange 180 desirably provides a predetermined shaped and is the corresponding "key." Together the key and key-hole provide a lock assembly. Once the key is inserted into the key-hole and rotated, the flange 180 no longer aligns with the opening 174 and the connector is "locked" to the base.

Figure 8:
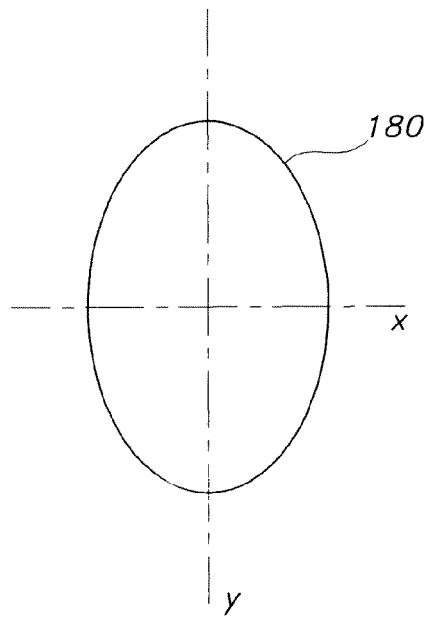
FIG. 8 is a plan view of the flange of FIGS. 3-7.

The elliptical flange 180 of this embodiment, if viewed alone and from above as shown in FIG. 8, has two axes of symmetry in the X-Y plane. This results in the flange 180 being insertable and removable from the opening 174 in two positions, 180 degrees from each other. This is true of any flange 180 having two axes of symmetry. While this makes accidental removal of the flange 180 from the opening 174 less likely and the connection more secure than that of prior devices, there still remains a small degree of risk that the feeding tube may become disconnected through the movement of the patient, during sleep for example. Alternate embodiments reducing this risk even further are provided below.

Figure 9:
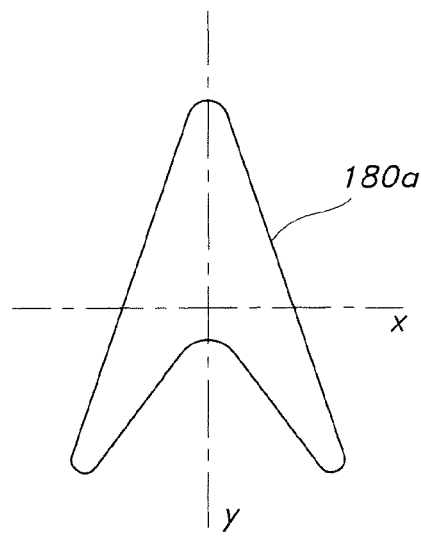
FIG. 9 is a plan view of the flange of another embodiment.

FIG. 9 shows a flange 180a that may be inserted in only one position. In the case of FIG. 9, the flange 180a has one axis of symmetry. In this FIG. 9 the flange 180a is of an arrowhead or triangle shape, though any other flange having one axis of symmetry would function similarly. Accordingly, an egg-shaped, pentagonal, heptagonal or other shape flange having one axis of symmetry in the X-Y plane is intended to be within the scope of the claims.

Figure 10:
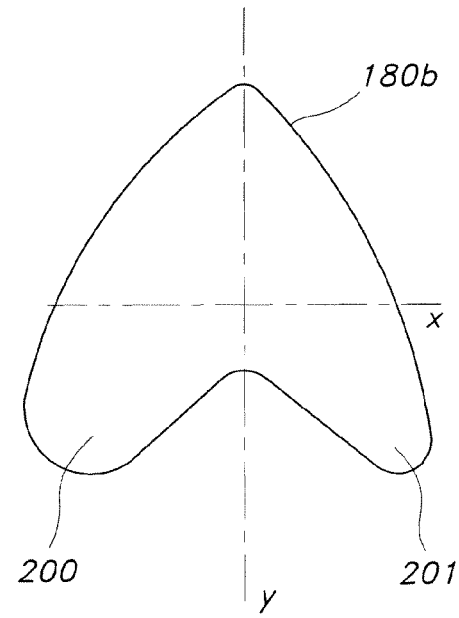
FIG. 10 is a plan view of a flange of another embodiment.

A single axis of symmetry is not required, however, for the flange to be insertable in only one position. FIG. 10 shows a flange 180b similar to that of FIG. 9. The lower lobes 200, 201 of the flange 180b are of different sizes, however, giving this flange 180b no axes of symmetry in the X-Y plane. Other designs for such asymmetric flanges are suitable as well.

A single position for insertion of the connector provides a large range of rotation for the feeding set head prior to the flange being in a position to be withdrawn; e.g. 360 degrees. This allows the user to be less concerned about accidental disconnection and the accompanying negative consequences. Depending on the placement of the detents, discussed below, the connector may rotate through an angle greater than 300 degrees prior to contacting the detents; e.g. 310 degrees, 330 degrees and 345 degrees.

Figure 11:
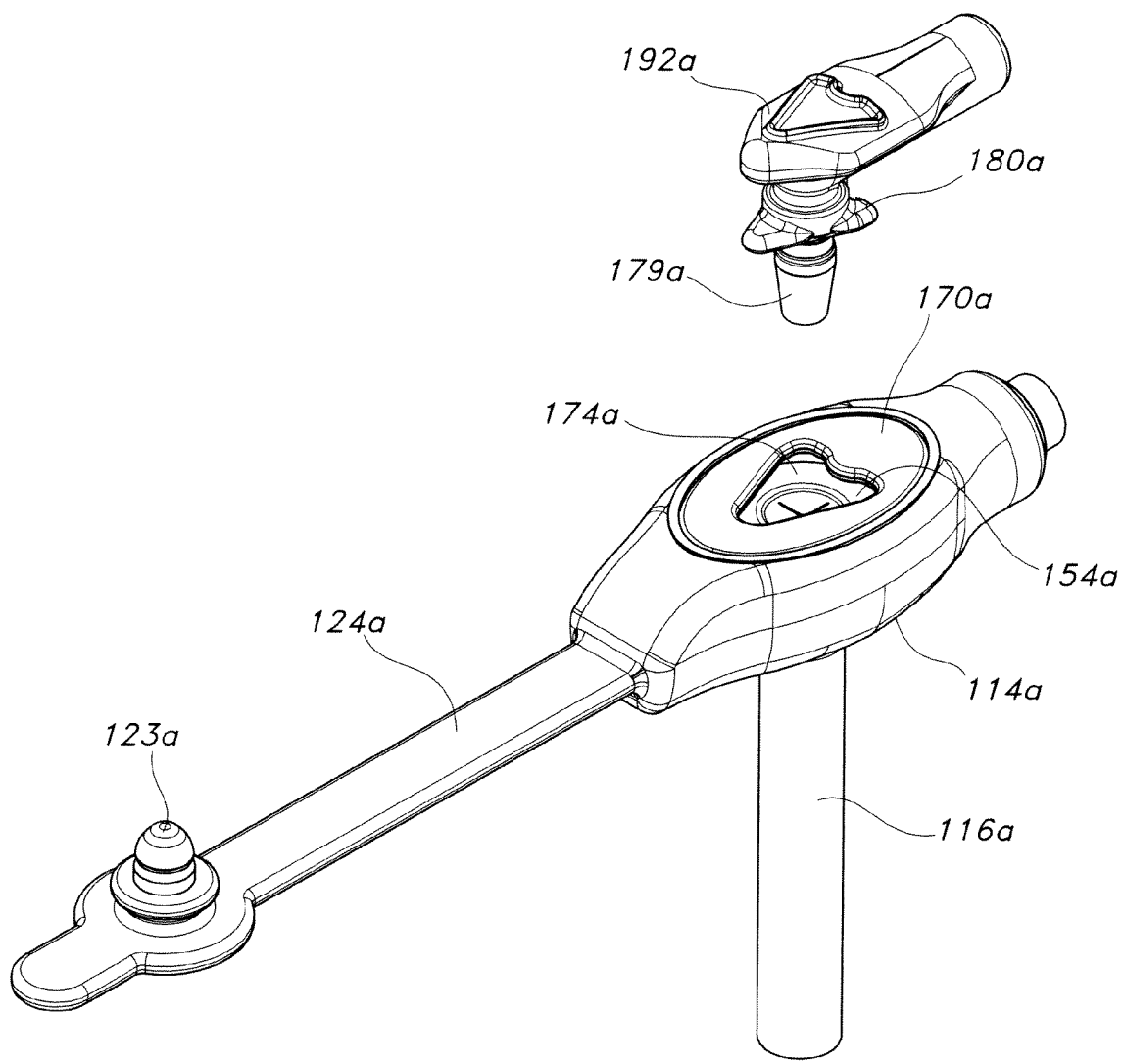
FIG. 11 shows a flange having one axis of symmetry in conjunction with a base and feeding set connector.

FIG. 11 shows the flange 180a having one axis of symmetry, along with its respective opening 174a, base 114a and catheter 116a. It may clearly be seen that this flange may only be inserted in one position. The connector illustrated in FIG. 11 also has an arrow shaped thumb landing 192a that helps indicate the position of the flange tactilely.

Figure 12:
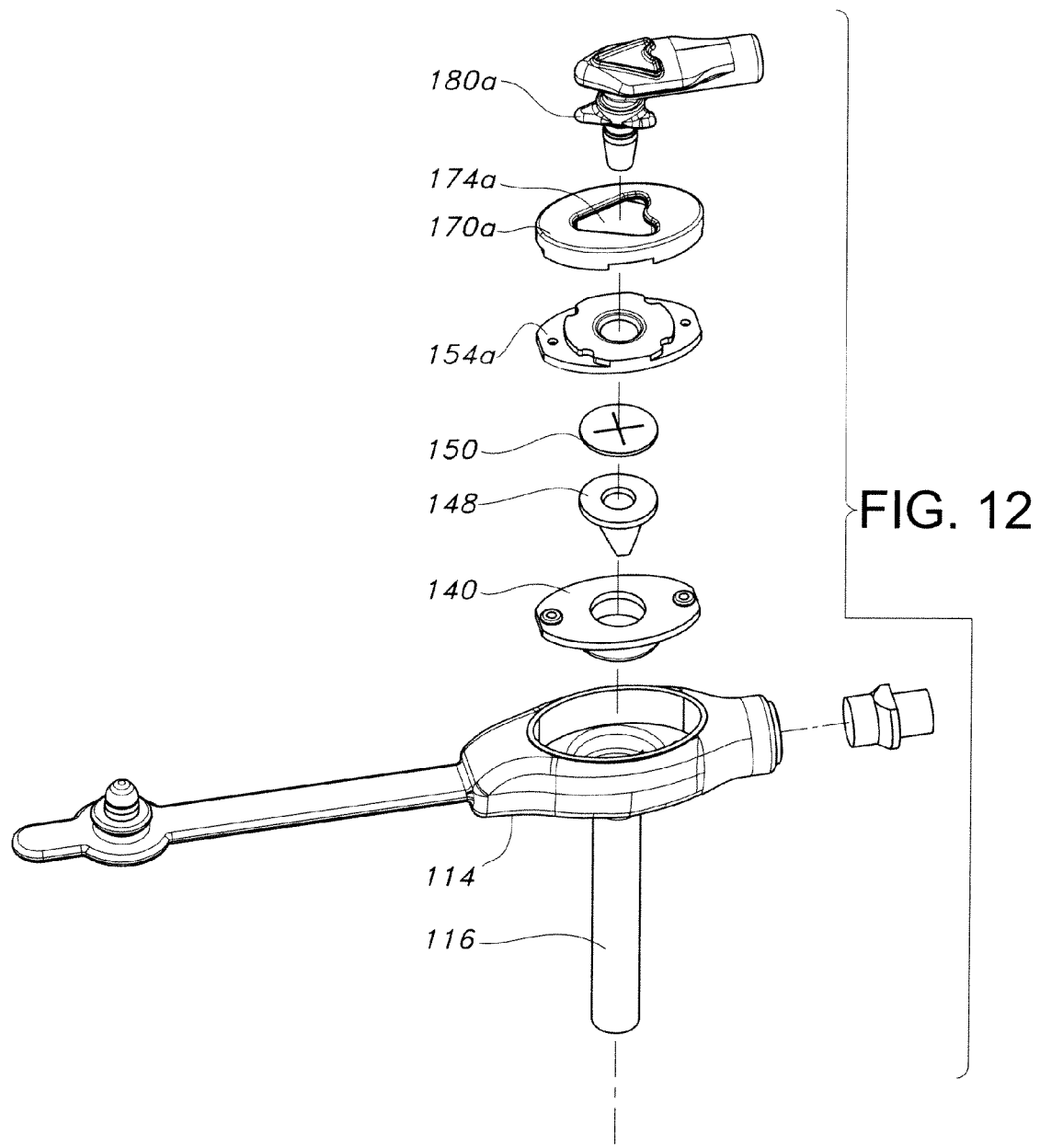
FIG. 12 is an exploded perspective view of the enteral feeding assembly base and connector of FIG. 11.

As discussed above, the base, locking mount and mount cover(s) must, of course, be shaped to match the shape of the flange. The parts distal to the locking mount, in contrast, may be substantially the same for any flange design. I.e., the parts in FIG. 3 below the locking mount 154 may be substantially the same for any flange design. FIG. 12 is an exploded perspective view of the enteral feeding assembly base and connector of FIG. 11. The parts distal to the locking mount 154a are the same as in FIG. 3. The locking mount 154a in this embodiment has a slightly raised center to accommodate the valve 148 and diaphragm 150. This is a slightly different shape than that of the locking mount 154 shown in FIG. 3, however, the function is equivalent to the locking mount 154 shown in FIG. 3. The mount cover 170a (shown separately in FIG. 13) is shaped to complement the flange 180a and has the appropriately shaped opening 174a for the flange 180a.

Figure 13:
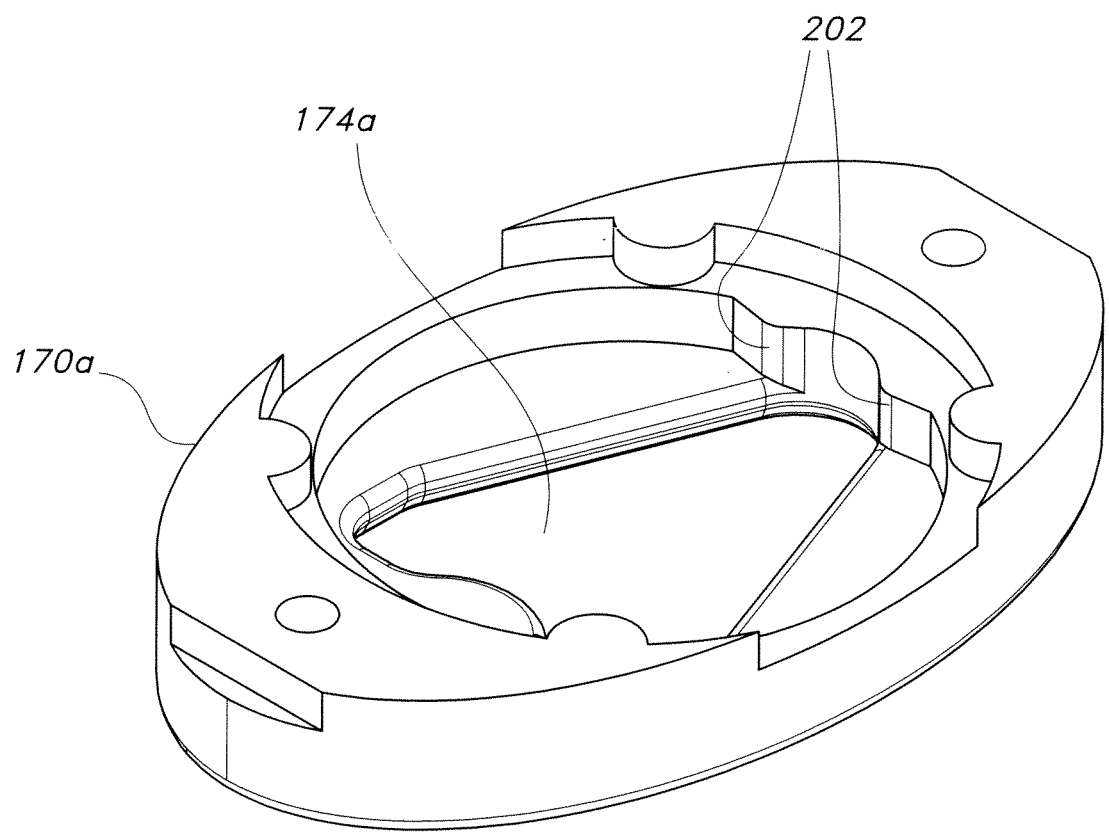
FIG. 13 shows an inverted view of the mount cover of FIG. 12.
Figure 14:
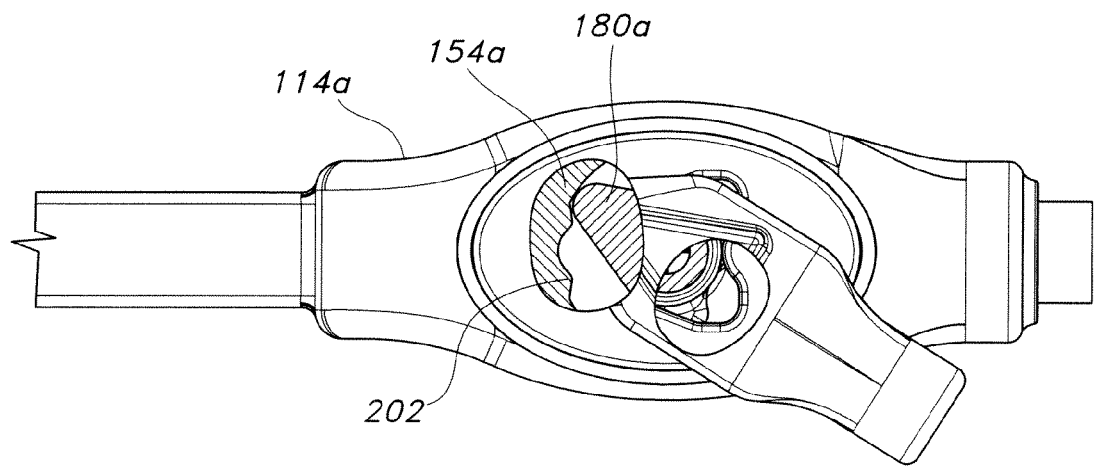
FIG. 14 is a view of the connector attached to the base, with a cut-out portion to allow a view inside the base to the locking mount.

Another aspect of this disclosure is a feature that may be used with any embodiment or design of flange. The feature is a "detent" that provides resistance to rotation and so tactilely informs the user that the flange is approaching the removal position. FIG. 13 shows a view of the mount cover 170 from below. The detents 202 are clearly visible in this view, as is the opening 170a. FIG. 14 is a view of the connector 180a attached to the base 114a, with a cut-out portion to allow a view inside the base 114a to see the detents 202 on the mount cover 170a. The mount cover 170a has protrusions or detents 202 on either side of the position where the tip of the arrowhead-shaped flange 180a would be upon insertion or for removal, though the detents may be located such that they contact other parts of the flange 180a rather than the tip. As the user rotates the connector, he can feel resistance from either direction just before the connector gets to the removal position. As mentioned above, this may provide greater than 300 degrees of rotational movement for the connector relative to the base. Further, when the position of the "key" relative to the "key hole" can be tactilely felt or determined by a user's hands, it is easier for a patient to lock and unlock a feeding set connector from the enteral feeding assembly base. This is also true when it is dark and the user does not want to turn on a light. Further, due to the position of the enteral feeding assembly on a patient's body, it may be difficult for the patient to see the proximal surface of the base of the enteral feeding assembly. A connection and disconnection which can be made tactilely, without needing a mirror, light or another person's assistance, is very desirable.

It has been found that a force or torque that desirably should be applied to move the flange 180 past a detent 202 is from a positive amount to 25 ounce-inch (17.65 N-cm). More particularly the force should be from a positive amount to 10 ounce-inch (7.06 N-cm), more particularly between a positive amount and 5 ounce-inch (3.5 N-cm), and still more particularly between 3 and 5 ounce-inch (2 and 3.5 N-cm). These amounts of force provide the user with enough resistance to inform the user that the detent has been overcome but are not so great as to make it impossible or very difficult to overcome the resistance of the detent. The amount of force needed to overcome the detent may be adjusted by making the detent protrude a greater distance or by making the detent and/or flange from harder materials, and such adjustments are within the ability of those skilled in the art.

Figure 15:
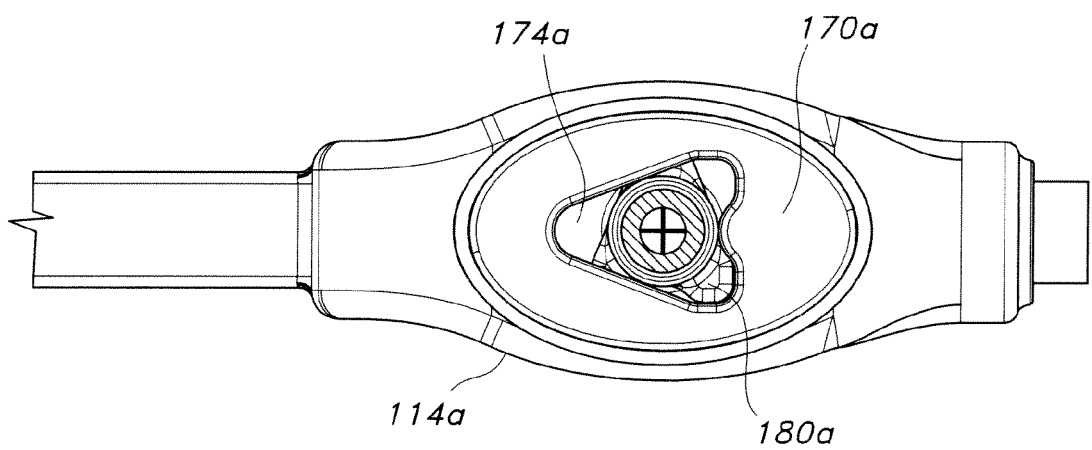
FIG. 15 illustrates the arrowhead flange of FIG. 9 without any proximal items and as it appears when inserted into the opening and turned.

Still another aspect of the flange is that, once inserted and turned, it desirably has at least two points of contact with the lower surface of the mount cover 170 (i.e., the proximal side of the base) at all times. FIG. 15 illustrates the arrowhead flange 180a without any proximal items and as it appears when inserted into the opening 174a and turned. As shown, at least two lobes of the flange 180a are in contact with the distal side of the mount cover 170a. This helps to keep the connector stable and aligned properly within the base.

It will be understood that some components may be formed as one component, or more components than are shown. Further, more, fewer, or different valves may be used. Other changes, alterations, combinations, and so forth, are intended as enabled by the example embodiments illustrated and/or described herein.

What is claimed is:

1. An enteral feeding assembly with a lock assembly, comprising:
    a base configured to be disposed on a skin surface of a patient, the base having a distal surface configured to be positioned adjacent a skin surface, the base including an uppermost horizontal proximal surface having a key-hole opening with a predetermined non-circular shape formed therein and the base including a space formed below the proximal surface of the base, the space extending radially outward of the key-hole opening below the proximal surface of the base;
    a catheter carried by the base and having a lumen formed therethrough which is in communication with the proximal opening in the base, a portion of the catheter extending distally away from the distal surface of the base, at least a portion of the distal end of the catheter configured to be positioned in a body lumen;
    a feeding set connector disconnected and removed from said base, said connector axially insertable from above into the key-hole opening in the proximal surface of said base for use of said enteral feeding assembly to supply liquid nutrients to said body lumen, said connector including a flange key and a cuff extending from the flange key, and an opening formed through the feeding set connector, flange key and cuff;
    wherein the flange key has a predetermined non-circular circumferential shape that matches the predetermined non-circular shape of the key-hole opening in the proximal surface of the base so that the flange key moves vertically through the key-hole opening and into the space below the proximal surface of the base when the feeding set connector is at a rotational position such that the noncircular key flange is aligned with the non-circular key-hole opening, and the flange key is rotatable within the space between a locked position and an unlocked position relative to the base to connect said feeding set connector to said base, in the locked position, the flange key engaging against an underside of the proximal surface such that the feeding set connector cannot be pulled away from the base;
    wherein when the flange key is positioned within the base, the flange key can rotate through an angle of at least 90 degrees without becoming unlocked, and;
    when the flange key is positioned within the base, the cuff extends through the opening in the base and is in fluid communication with the lumen of the catheter so that liquid nutrients connected by tubing to said feeding set connector move through the feeding set connector and through the catheter lumen to said body lumen; and
    at least one detent defined in the base at a location relative to the unlocked position of the flange key such that, upon being rotated to the unlocked position, the flange key engages the detent thereby providing a tactile indication of increased resistance to rotation of the flange key prior to the flange key being rotated to the unlocked position.

2. The enteral feeding assembly of claim 1 wherein said flange key is engaged against said detent to such an extent that a force of between a positive amount and 3.5 N-cm is required to overcome resistance and rotate said flange key past said detent.

3. The enteral feeding assembly of claim 1, wherein the base is a low profile base configured to be positioned on a skin surface of a patient.

4. The enteral feeding assembly of claim 1, wherein the flange key has one axis of symmetry in an X-Y plane.

5. The enteral feeding assembly of claim 1, wherein the flange key is shaped like an arrowhead.

6. The enteral feeding assembly of claim 1, wherein the flange key has no axis of symmetry in an X-Y plane.

7. The enteral feeding assembly of claim 1, wherein the flange key has at least two points of contact with a lower surface of the proximal side of the base at all times after entering the space below the opening and being rotated.

8. The enteral feeding assembly of claim 1, wherein the connector may rotate up to 360 degrees after connection to the base.

9. The enteral feeding assembly of claim 1, wherein the connector rotates between 300 and 345 degrees after connection to the base prior to the flange key engaging the at least one detent.

10. A method of using a lock assembly with an enteral feeding assembly, comprising:
    providing an enteral feeding assembly, including
    a base configured to be disposed on a skin surface of a patient, the base having a distal surface configured to be positioned adjacent a skin surface, the base including an upper horizontal proximal surface having an opening formed therein;
    a catheter carried by the base and having a lumen formed therethrough which is in communication with the opening in the base, a portion of the catheter extending distally away from the distal surface of the base, at least a portion of the distal end of the catheter configured to be positioned in a body lumen;
    wherein the base includes a key-hole opening formed through a portion of the proximal surface, the key-hole opening having a predetermined non-circular shape, the base including a space formed below the proximal surface of the base, the space extending radially outward of the key-hole opening in the proximal surface;
    providing a feeding set connector disconnected and axially separated from said base, said feeding set connector including a flange key having a predetermined non-circular circumferential shape matching the predetermined non-circular shape of the key-hole opening and a cuff extending from the flange key, and an opening formed through the feeding set connector, flange key, and cuff,
    inserting the feeding set connector vertically into the base by positioning the flange key of the feeding set connector through the key-hole opening in said base and into the space below the proximal surface to connect the feeding set connector to the base;
    locking the flange key into a position relative to the base by rotating said connector such that the key flange engages against an underside of the proximal surface, the flange key able to rotate through an angle of at least 90 degrees without becoming unlocked, the cuff extending through the opening in the base and in liquid communication with the lumen of the catheter so that liquid nutrients connected by tubing to the feeding set connector move therethrough and through the catheter lumen to a body lumen; and
    unlocking the flange key from the base by rotating the flange key to an unlock position, wherein at least one detent is defined in the base at a location relative to the unlock position such that the flange key engages the detent prior to reaching the unlock position, thereby providing a tactile indication of increased resistance to rotation of the flange key prior to the flange key being rotated to the unlock position.

11. The method of claim 10 further including the step of un-locking the flange key and removing the feeding set connector from the base.

\* \* \* \* \*